United States Patent
Mauro et al.

(10) Patent No.: US 9,090,922 B2
(45) Date of Patent: Jul. 28, 2015

(54) PROCESS FOR THE PREPARATION OF NEBIVOLOL

(75) Inventors: Sandro Mauro, Rome (IT); Daniela Fattori, Velletri (IT); Piero D'Andrea, Genzano di Roma (IT); Amalia Cipollone, Rome (IT); Enzo D'Andrea, Genzano di Roma (IT); Carmela Ercolano, Genzano di Roma (IT)

(73) Assignee: MENARINI INTERNATIONAL OPERATIONS LUXEMBOURG S.A., Luxembourg (LU)

( * ) Notice: Subject to any disclaimer, the term of this patent is extended or adjusted under 35 U.S.C. 154(b) by 0 days.

(21) Appl. No.: 13/990,220

(22) PCT Filed: Nov. 30, 2011

(86) PCT No.: PCT/IB2011/055385
§ 371 (c)(1),
(2), (4) Date: Jun. 27, 2013

(87) PCT Pub. No.: WO2012/095707
PCT Pub. Date: Jul. 19, 2012

(65) Prior Publication Data
US 2013/0295622 A1 Nov. 7, 2013

(30) Foreign Application Priority Data
Nov. 30, 2010 (IT) .............................. RM2010A0622

(51) Int. Cl.
*C12P 17/16* (2006.01)
*C07D 311/58* (2006.01)

(52) U.S. Cl.
CPC .............. *C12P 17/162* (2013.01); *C07D 311/58* (2013.01)

(58) Field of Classification Search
None
See application file for complete search history.

(56) References Cited

U.S. PATENT DOCUMENTS

| 5,037,747 A | * | 8/1991 | Coffen et al. | ............... 435/125 |
| 5,912,164 A | | 6/1999 | Warneck et al. | |
| 7,560,575 B2 | | 7/2009 | Bader et al. | |

FOREIGN PATENT DOCUMENTS

EP 1 803 715 7/2007

OTHER PUBLICATIONS

Int'l Search Report for PCT/IB2011/055385, three pages, mailed Mar. 1, 2012.
Written Opinion for PCT/IB2011/055385, six pages, mailed Mar. 1, 2012.
Int'l Preliminary Report on Patentability for PCT/IB2011/055385, 13 pages, mailed Sep. 28, 2012.

* cited by examiner

*Primary Examiner* — Kade Ariani
(74) *Attorney, Agent, or Firm* — Nixon & Vanderhye PC

(57) ABSTRACT

The present invention relates to a novel process for the synthesis of the Nebivolol product depicted in Scheme 1, comprised of a reduced number of high-yield steps, and characterized by the enzymatic resolution of the chroman ester precursor.

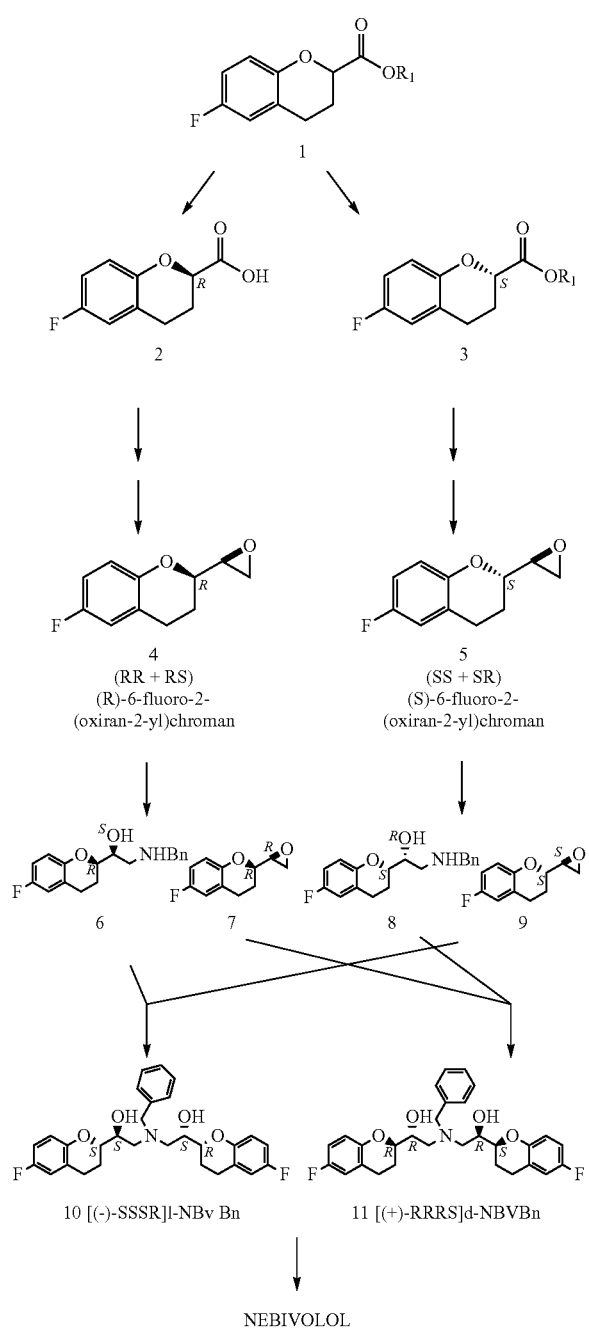

16 Claims, No Drawings

PROCESS FOR THE PREPARATION OF NEBIVOLOL

This application is the U.S. national phase of International Application No. PCT/IB2011/055385, filed 30 Nov. 2011, which designated the U.S. and claims priority to IT Application No. RM2010A000622, filed 30 Nov. 2010; the entire contents of each of which are hereby incorporated by reference.

FIELD OF THE INVENTION

The present invention relates to a novel process for the synthesis of Nebivolol.

Nebivolol is a racemic mixture of the two enantiomers [2S[2R[R[R]]]] α,α'-[imino-bis(methylene)]bis[6-fluoro-chroman-2-methanol] and [2R[2S[S[S]]]] α,α'-[imino-bis(methylene)] bis[6-fluoro-chroman-2-methanol] (FIG. 1).

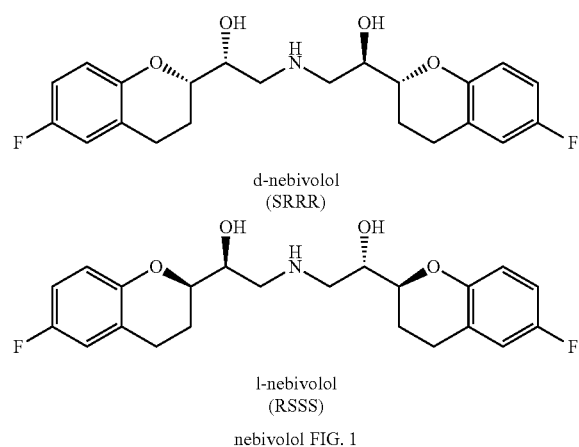

nebivolol FIG. 1

In particular, it is reported the enzymatic resolution of the starting chromanyl ester (1) by treatment with a stereoselective enzyme belonging to the family of esterases, in a native or recombinant form, obtainable also from the microorganism *Ophiostoma novo-ulmi*.

The esters and acids thus obtained can be converted, by processes known to a person skilled in the art, into the corresponding "semichiral" epoxides, i.e. the pairs (RR+RS, 4) and (SS+SR, 5) of Scheme (1).

In turn, the components of each pair can be separated by exploiting their different reactivity with benzylamine in a solvent consisting of a tertiary alcohol. Under these conditions of kinetic resolution, the epoxides RS and SR will be converted into the corresponding opening products (6 and 8), whereas the epoxides RR and SS will remain unaltered.

The epoxide RR (7) is then separated from amine RS (6) and the epoxide SS (9) is separated from amine SR (8) with processes known to a person skilled in the art and preferentially by crystallization of the basic component.

Then, the amine RS is reacted with the epoxide SS to obtain l-benzylnebivolol. Likewise, the amine SR is reacted with the epoxide RR to obtain d-benzylnebivolol.

The l- and d-benzyl Nebivolol thus obtained are pooled in equimolar amounts, crystallized and converted into Nebivolol HCl according to processes known to a person skilled in the art.

STATE OF THE ART

Nebivolol is known as an adrenergic beta-receptor antagonist, an antihypertensive agent, a platelet aggregation inhibitor and a vasodilating agent.

Nebivolol has basic properties and may be converted into an acceptable pharmaceutical salt form by treatment with an acid. The hydrochloride salt is the marketed form.

Nebivolol contains four asymmetric centres, and therefore 16 stereoisomers are theoretically possible. However, because of the particular structure of the molecule (the presence of an axis of symmetry), only 10 stereoisomers can actually be formed (Scheme 2).

SCHEME 2

Possible stereoisomers for Nebivolol

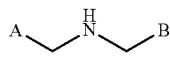

B =

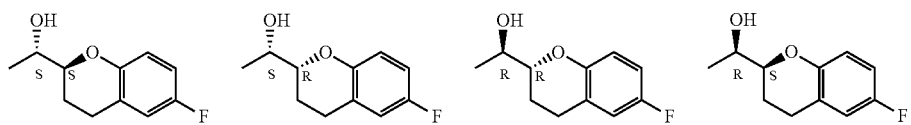

A =

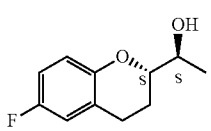

| | SSSS | SSSR (l-nebivololo) | SSRR | SSRS |

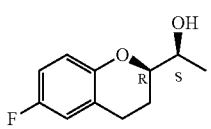

| | RSSS (= SSSR) | RSSR | RSRR | RSRS |

SCHEME 2-continued

Possible stereoisomers for Nebivolol

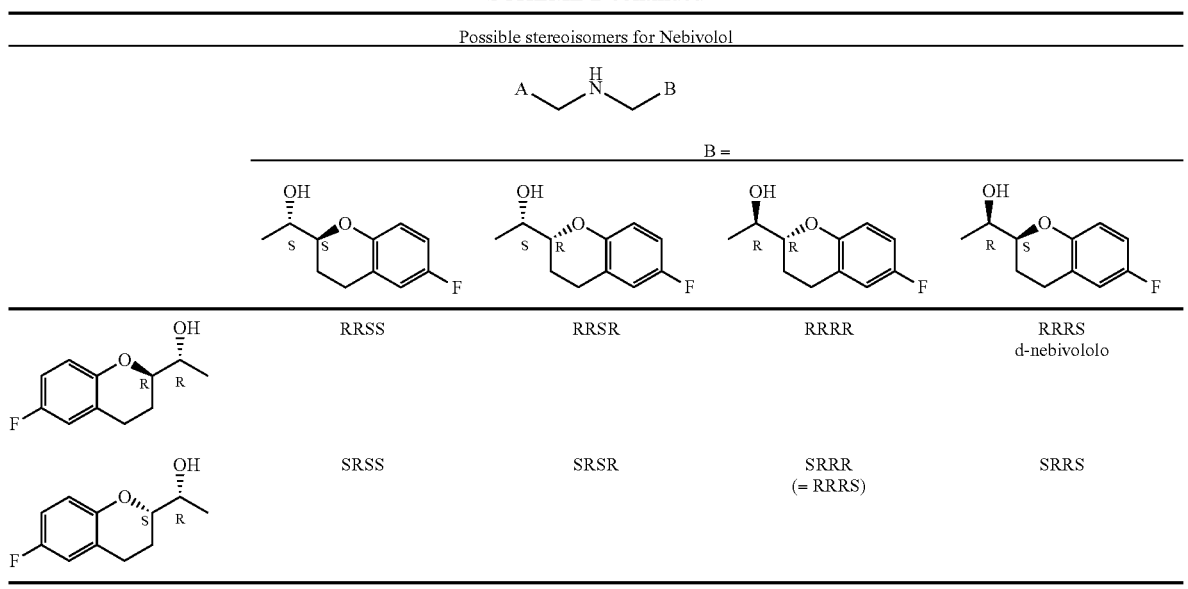

In fact, because of the symmetry of the molecule, RSSS=SSSR, RRSS=SSRR, SRSS=SSRS, RRSR=RSRR, SRSR=RSRS and RRRS=SRRR.

U.S. Pat. No. 4,654,362 (EP 0145067, Janssen) describes the synthesis of products of Nebivolol series with use of epoxide isomers as key intermediates in the synthesis. The products are obtained sometimes in mixture and sometimes enantiopures, without defining the absolute configuration. In particular, example 84 of said patent describes the obtainment of a mixture of isomers as defined in Scheme 3.

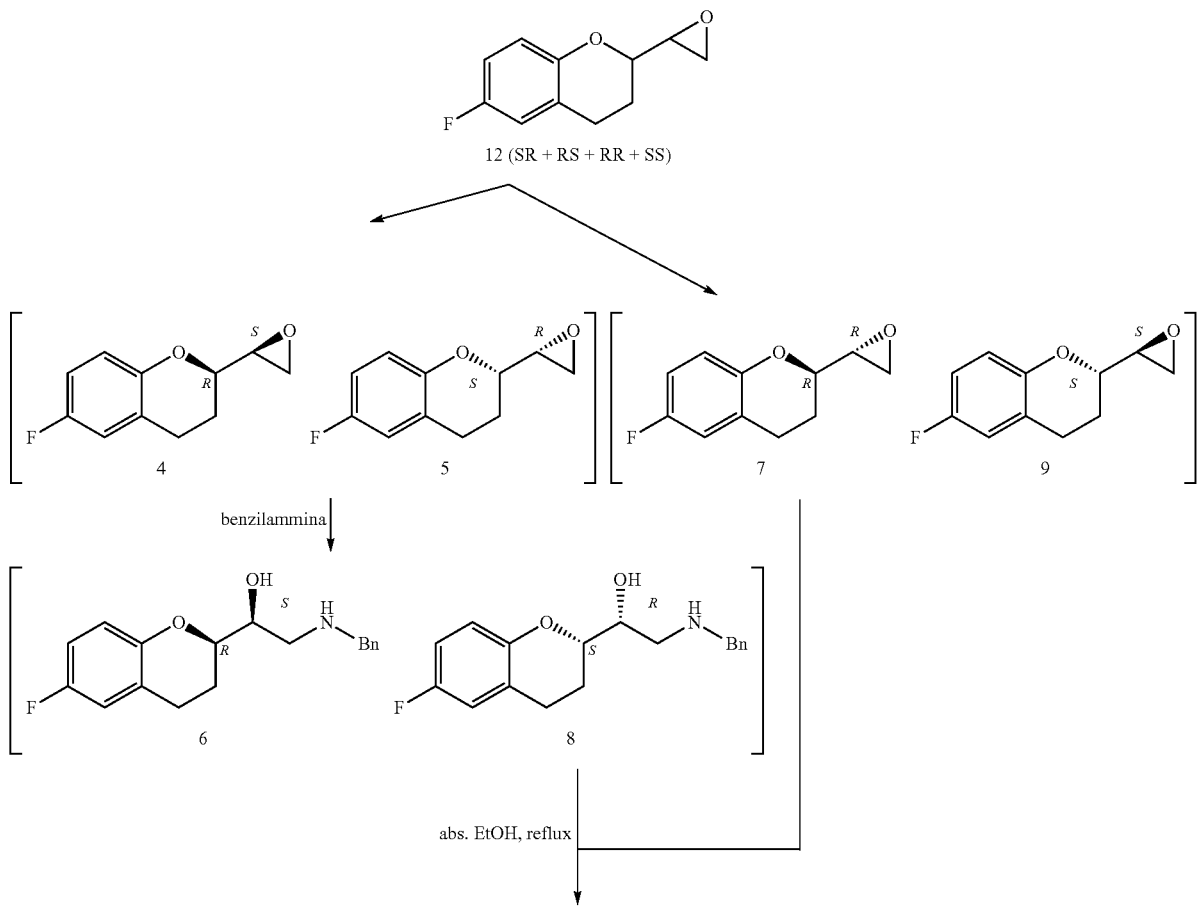

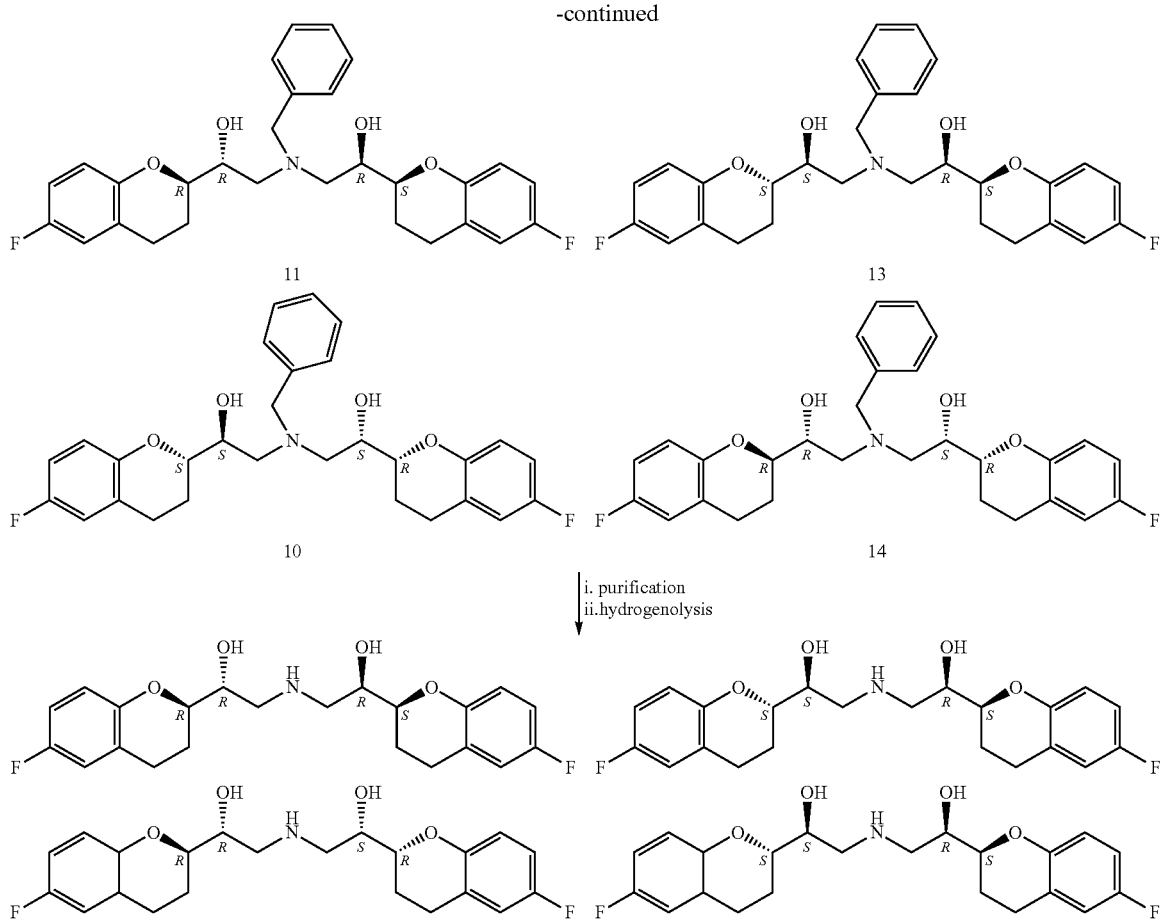

These are separated, with a chromatography column, into the two epoxide racemates (RS/SR, 4/5) and (RR/SS, 7/9). There follow the opening of a pair of epoxides (4+5) with benzylamine and the use of the products of said reaction (6+8) to open the second pair of epoxides (7+9). This operation leads to the production of the 4 benzylated diastereoisomers (10-14).

EP 0334429 (Janssen) describes the same process reported in EP 0145067, but with more experimental details and with attention focused on the preparation of a single isomer of Nebivolol. In this case, specifically 6-fluorochroman carboxylic acid is resolved into the individual enantiomers by treatment with (+)-dehydroabiethylamine. The individual enantiomers thus obtained are converted into the corresponding semichiral epoxides according to the following synthetic scheme (isomer S shown):

Scheme 4

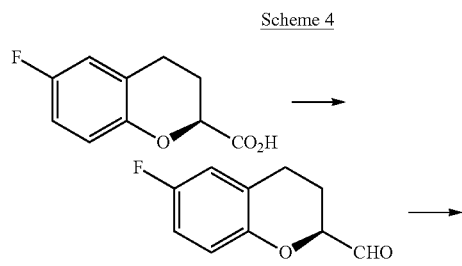

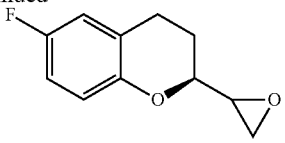

A stereoselective synthesis of isomer [2R,αS,2'S, α'S]-α, α'-[iminobismethylene]bis[6-fluoro-3,4-dihydro-2H-1-benzopyran-2-methanol] is described.

The process for the resolution of acid esters used suffers from several drawbacks for what concerns its industrial application. In fact, additional steps (amide forming, fractionated crystallization, amide hydrolysis) are introduced, and moreover the overall yield is rather low. The mixture of diastereoisomeric epoxides thus obtained is run on preparative HPLC to isolate the isomer of desired chirality.

Hetero Drugs Limited, in WO 2006/016376 and in the subsequent WO 2007/083318, describes fractionated crystallization processes applied at the level of the diastereoisomeric mixture (10, 11, 13, 14) of benzyl Nebivolol, which lead, in this case as well, to a discarding of about 50% of the starting material, related to the need to remove unwanted diastereoisomers.

WO 2007/041805 (Egis Gyógyszergyár) describes a process for the preparation of [2S*[R*[R*[R*]]]] and [2R*[S*[S*[S*]]]]-(±)-α,α'-[iminobis(methylene)]bis[6-fluoro-3,4-dihydro-2H-1-benzopyran-2-methanol] and its individual pure [2S*[R*[R*[R*]]]] and [2R*[S*[S*[S*]]]] enantiomers starting from very different compounds. The steps used for Nebivolol synthesis as mixture of enantiomers are about thirty, making the synthesis very lengthy and uneconomic (Scheme 5).

Scheme 5

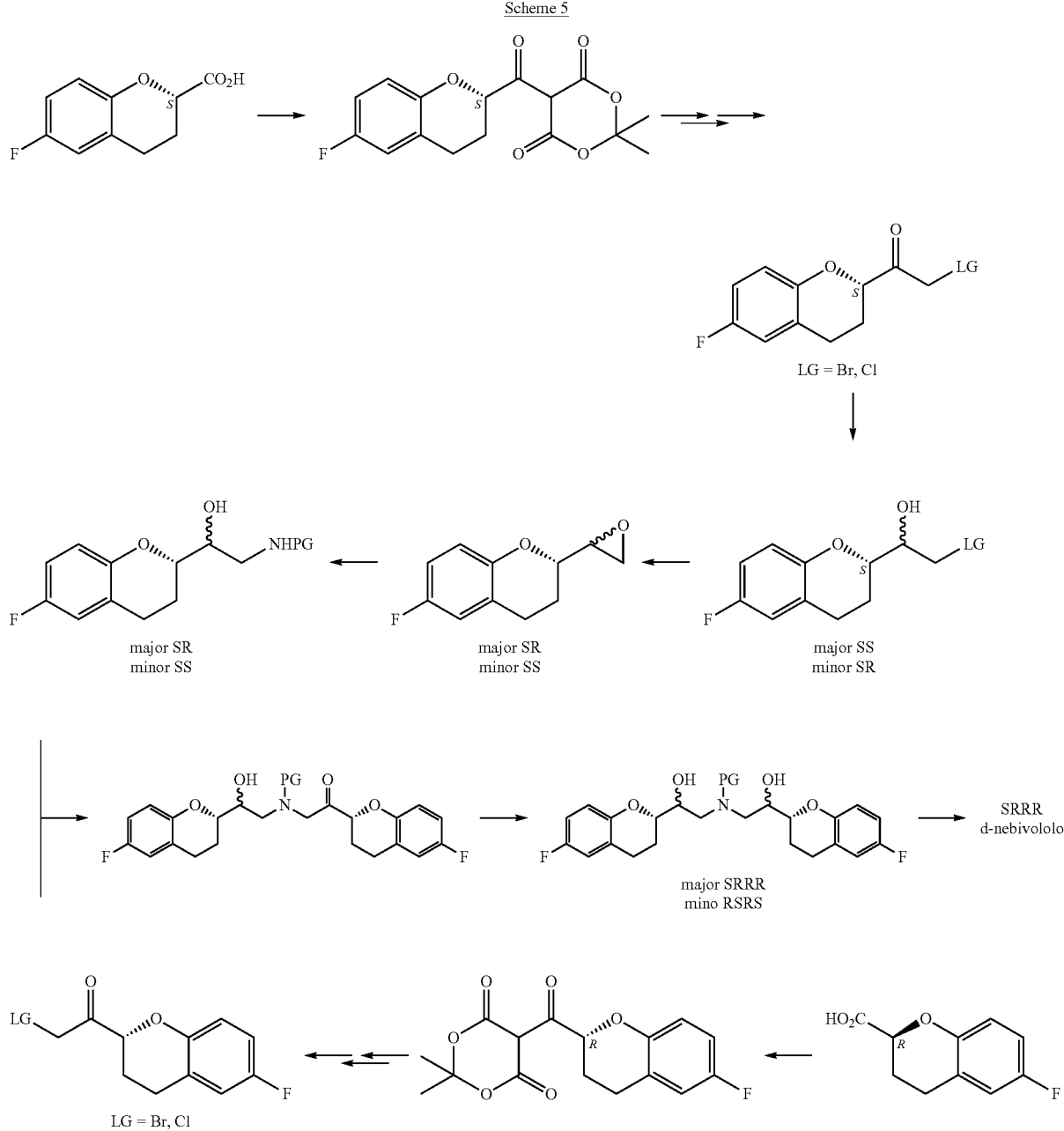

In WO 2008/010022 (Cimex Pharma) a route is reported that, starting from 6-fluoro chroman carboxylic acids resolved according to processes in the literature, leads to the synthesis of the two Nebivolol enantiomers according to two separate sequences (Scheme 6, for d-Nebivolol).

In the opening of epoxides by a benzylamine, a single opening product crystallizes from the reaction mixture, but the other diastereoisomer is removed with the mother liquors, leading in this case as well to the elimination of a considerable fraction of material in an already quite advanced stage of the synthetic sequence. In addition, the last chiral centre is added at the penultimate step by reduction of a ketone, quite a sensitive reaction, which in order to obtain optimal results envisages the use of $KBH_4$ and titanium isopropoxide.

WO2008/064826 (Zach System) reports a process for the resolution of epoxides, once the pairs of diastereoisomers (RS/SR and RR/SS) have been separated chromatographically, through the enantioselective opening of the same epoxides mediated by chiral complexes of cobalt II (Scheme 7). In this case a chromatographic separation step is necessary, less than practical from the standpoint of the process, while cobalt complexes require caution in manipulation and disposal.

Scheme 6

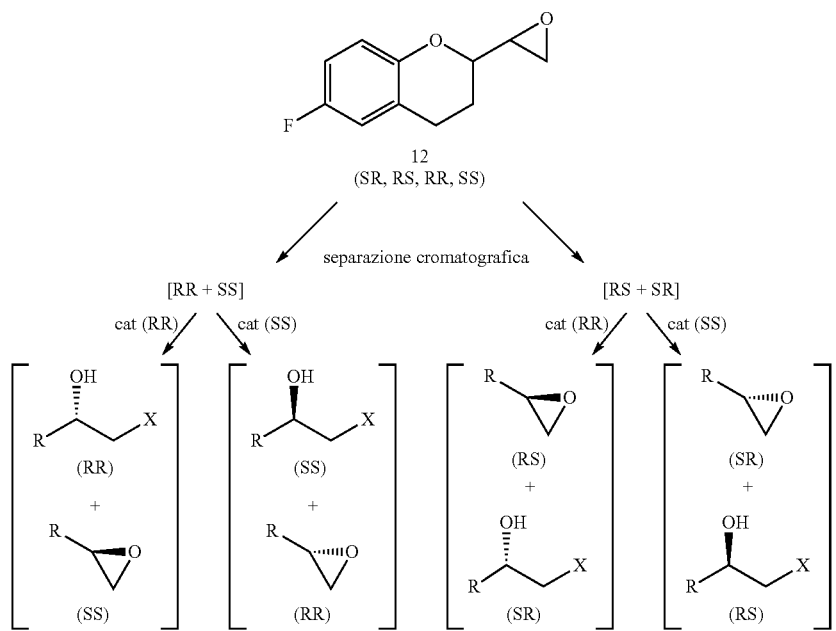

WO 2008/064827 (Zach System) describes the separate and enantioselective synthesis of d- and l-Nebivolol starting from the two optical isomers of the protected glyceraldehyde, such as 2,2-dimethyl acetale (Scheme 7). The diastereoisomers are separated with processes known, but not described. The number of synthetic steps is higher than that of classic synthesis, while aldehyde precursors are known as compounds not overly stable, which tend to polymerize when stored in a pure form and at room temperature.

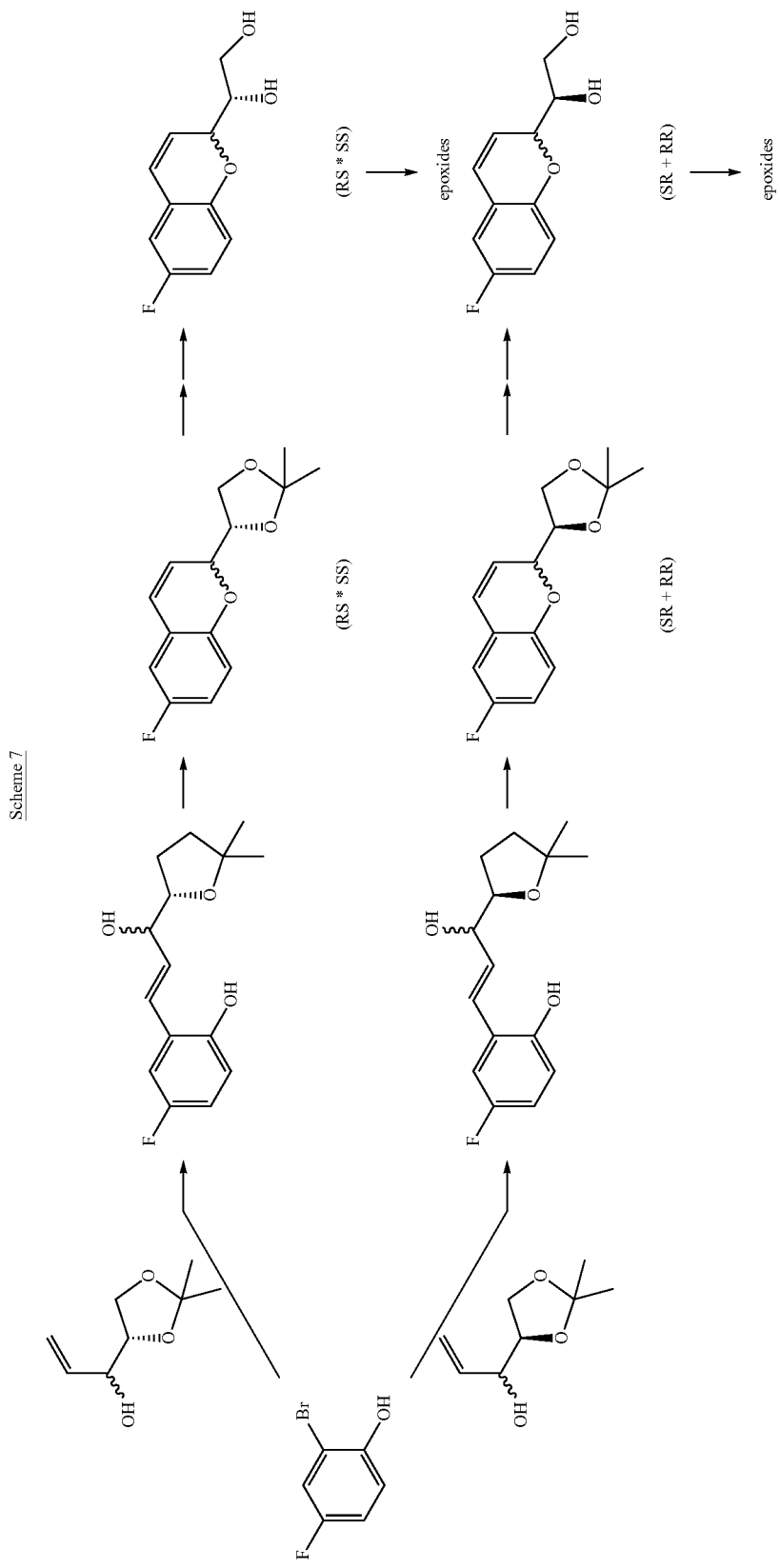
Scheme 7

As to enantiomer separation at the level of the 6-fluoro-chroman-2-carboxylic acid, it is known that the process for amide formation with (+)-dehydroabiethylamine, followed by fractional crystallization and amide hydrolysis to recover the acid (EP 0334429), is toilsome and affords rather low yields.

Concerning the enzymatic resolution of esters of carboxylic acids, this is a process known in the literature, but it had never been employed on esters of fluorine derivatives of chroman-2-carboxylic acids, nor consequently used for Nebivolol synthesis.

Specifically, known examples related to chroman-2-carboxylates are reported.

In U.S. Pat. No. 5,037,747, (2R)-hydroxy-substituted benzopyran-2-carboxylic esters and (2S)-hydroxy-substituted benzopyran-2-carboxylic acids are prepared by the Pseudomonas lipase-catalyzed selective hydrolysis of the corresponding racemate.

Urban (U.S. Pat. No. 5,089,637, EP 0448254) exploits an enzymatic hydrolysis with an esterase derived from Pseudomonas fluorescens to resolve racemic mixtures of general formula (I), where $R=C_1-C_3$ alkyl.

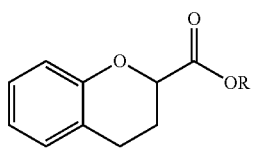

(I)

WO 96/40975 reports the use of a microbial esterase derived from Serratia marcescens for the resolution of chroman-2-carboxyl alkyls of the same general formula, but with $R>C_3$.

In DE 4430089 it is reported a series of examples in which chroman-2-carboxyl esters are subjected to enzymatic hydrolysis with a selected group of enzymes (chymotrypsin, lipase from Candida lipolytica, lipase from Aspergillus oryzae, lipase from Geotrichum candidum, lipase from Aspergillus niger).

Finally, as to the esterase derived from Ophiostoma novo-ulmi ascomycete, the details related to its isolation, cloning in E. Coli and to its use in the resolution of esters are reported, e.g., by M. N. Isupov et al. in Acta Crystallographica—Biological Crystallography Section D60, p. 1879-1882 (2004), or in EP 0687305, while an use thereof in the resolution of enantiomers of arylalkanoid acids and, more specifically, of ketoprofen, is described in EP 0693134.

On the basis of literature evidence available to date, Nebivolol synthesis still entails numerous synthetic problems. The original Janssen synthesis going through the epoxides (Scheme 3, mixture 6) is surely the shorter one, but requires a separation by preparative HPLC of the two diastereoisomeric epoxide pairs. The other processes generally envisage many more synthetic steps.

In a sizeable part of the synthesis reported, intermediate product percentages, which may arrive up to the 50%, are discarded to eliminate unwanted diastereoisomers that have unavoidably been produced in the synthetic sequence applied.

Therefore, the need to develop a novel synthetic process, suitable for industrial use and avoiding the use of chromatographic separations and the need to eliminate sizeable percentages of intermediate compounds though maintaining a limited number of synthetic steps, is markedly felt.

SUMMARY OF THE INVENTION

It has now surprisingly been found a more effective process for the synthesis of Nebivolol (Scheme 1) which allows to eliminate the drawbacks highlighted hereto for the synthesis routes previously known, i.e., it:

a) avoids, or considerably reduces, separation by preparative HPLC of the pairs (RR/SS RS/SR) of epoxides enantiomers or of other diastereoisomeric intermediates;

b) sensibly reduces the loss of product represented by undesired isomers, with a consequent increase of the overall yield.

The treatment of the mixture of the two enantiomers of the 6-fluorochroman-2-carboxylic acid ester is performed with a fungal esterase (lipase) obtainable from genus Ophiostoma. The preferred species is esterase from Ophiostoma novo-ulmi, already described in the literature for its stereoselective activity on the esters of naproxen or ketoprofen compounds.

The reaction carried out in an aqueous or aqueous/organic medium leads to hydrolysis to carboxylic acid of one of the two enantiomers in a selective manner, while the other one remains in the form of an ester. The reaction proceeds quickly and with a high stereoselectivity. The two compounds thus produced can be easily separated by acid-base extraction.

Therefore, object of the present invention is a process for the preparation of Nebivolol, the process comprising:

a. resolving, by an enzymatic hydrolysis reaction, the mixture of enantiomers of a 6-fluoro-2-carboxylic acid ester (1), wherein $R_1$ is a linear or branched $C_{1-5}$ alkyl group,

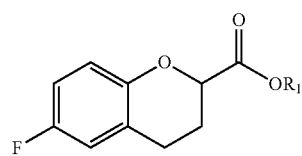

(1)

to give a mixture of acid (2) and ester (3)

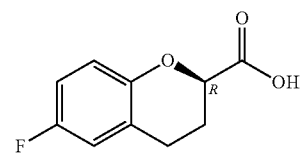

(2)

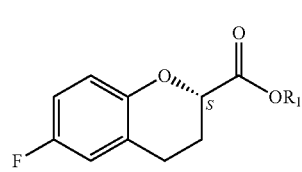

(3)

wherein the R acid (2) is present with an enantiomeric excess of >70% and the S ester (3) is present with an enantiomeric excess of >70%; the enantiomeric excess is preferably of >80%, and even more preferably of >90%, in both components;

b. using thus obtained acid (2) and ester (3) for the synthesis of the mixtures of epoxides (4) and (5),

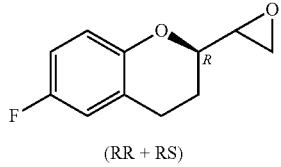

(RR + RS) (4)

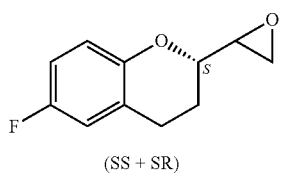

(SS + SR) (5)

c.1) The kinetic resolution reaction with benzylamine on the mixtures of epoxides (4) and (5) in a sterically hindered alcohol to obtain respectively the compounds (6)+(7) and (8)+(9) and their separation

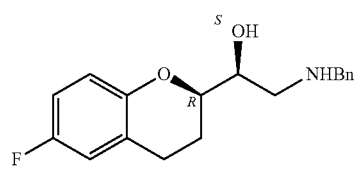

(6)

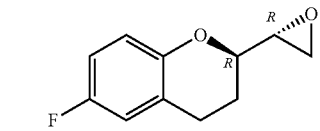

(7)

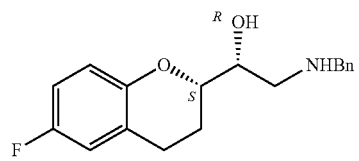

(8)

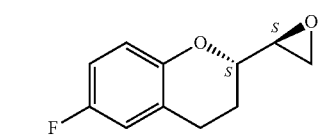

(9)

c.2) Alternatively to the kinetic resolution described at c.1), chromatographic separation of the mixtures of epoxides (4) and (5) and subsequent reaction of the RS epoxide with benzylamine to give the amino alcohol RS (6) and the epoxide SR with benzylamine to give the amino alcohol SR (8).

d. reacting the amino alcohol RS (6) with the epoxide (9) to obtain l-benzyl Nebivolol (10) and the amino alcohol SR (8) with the epoxide (7) to obtain d-benzyl Nebivolol (11)

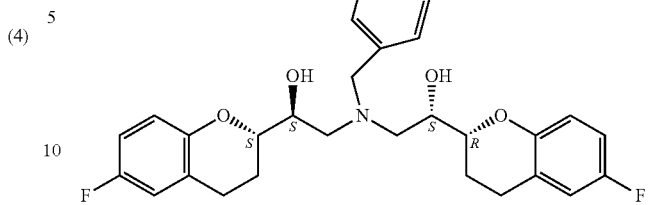

[(−)-SSSR] l-NBV Bn (10)

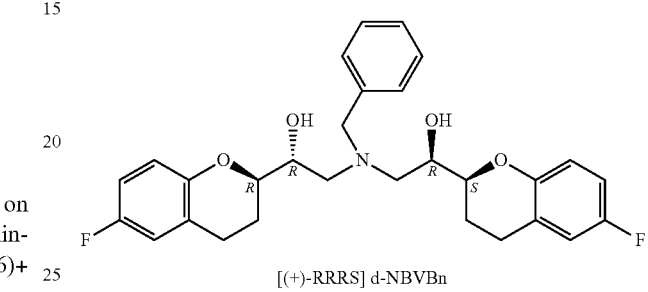

[(+)-RRRS] d-NBVBn (11)

e. deprotecting, with removal of the benzyl group with Nebivolol formation

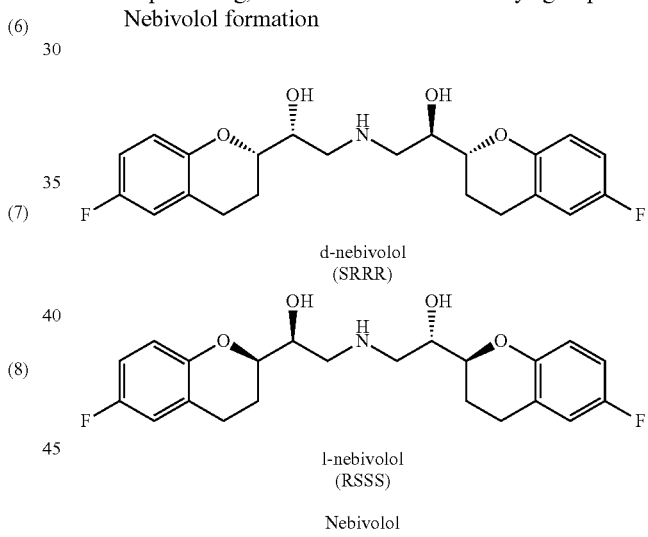

d-nebivolol
(SRRR)

l-nebivolol
(RSSS)

Nebivolol

To the ends of the present invention the group $R_1$, defined as a linear or branched $C_{1-5}$ alkyl group, represents a radical selected from: methyl, ethyl, propyl, isopropyl, butyl, sec-butyl, tert-butyl, amyl, tert-amyl; preferably it is a radical selected from methyl, ethyl, propyl, and even more preferably it is an ethyl group.

DETAILED DESCRIPTION OF THE INVENTION

According to the present invention, the Nebivolol compound is obtained with the process described in Scheme 1 starting from the racemic mixture of the 6-fluorochroman-2-carboxylic acid ester (1).

6-fluorochroman-2-carboxylate (1) may be resolved into its two enantiomers with high stereoselectivity through enantioselective hydrolysis catalyzed by a fungal esterase (lipase) obtainable from genus *Ophiostoma*. The preferred species is esterase from *Ophiostoma novo-ulmi*, already described in the literature for its stereoselective activity on the esters of naproxen or ketoprofen compounds.

The enzyme, in the form of an isolated and crystallized expression protein, is described by M. N. Isupov et al. in *Acta Crystallographica—Biological Crystallography* Section D60, p. 1879-1882 (2004). The enzyme is also described in EP-B1-0687305 (WO94/20634), EP-0693134, U.S. Pat. No. 5,912,164, and in EP1626093.

Enzyme expression in *E. coli* may be performed as described by M. N. Isupov et al. (supra) or in EP-B1-0687305 (WO94/20634).

This strain provides a good example of activity, however, given the rather diffused nature of activity in a wide variety of related strains, the scope of the invention is not meant to be limited only thereto. The microorganisms of genus *Ophistoma* and their enzymatic activity may be used to hydrolyze the racemic ester of 6-fluorochroman-2-carboxylated ethyl in a stereoselective manner, so as to bring to the acid, considerably enriched in enantiomer R., e.g. 93-100% of enantiomeric eccess with a 45-50% of conversion, and leave the enriched residual ester in the enantiomer S.

It is therefore produced the (R) 6-fluorochroman-2-carboxylic acid (2) with an enantiomeric excess of >70%, preferably of >80% and even more preferably of >90%, while the (S) 6-fluoro carboxylic acid remains in the form of an ester (3) with an enantiomeric excess of >70%, preferably of >80% and even more preferably of >90%.

The reaction may be conducted on any mixture of enantiomers, but generally the racemate is used.

The ester used for this reaction is a 6-fluoro-2-carboxylic acid ester (1), wherein $R_1$ is a linear or branched $C_{1-5}$ alkyl group, selected from the group comprised of methyl, ethyl, propyl, isopropyl, butyl, sec-butyl, tert-butyl, amyl, tert-amyl; preferably from methyl, ethyl, propyl and even more preferably from an ethyl group.

The reaction is preferably conducted at a pH 8-11, preferably 8.5-10.0.

The temperature may be comprised between 10 and 35° C., but preferably between 20 and 25° C.

The reaction mixture may be in an aqueous environment, or in the presence of water-immiscible solvents.

Recovery of both compounds is possible by processes known to a person skilled in the art and preferably through a series of acid-base extractions.

Both compounds are then used for Nebivolol synthesis (Scheme 1).

Through processes known to a person skilled in the art (by way of a non-limiting example, analogously to that described in WO2007041805) the acid (2) is transformed into the mixture of epoxides (RS) and (RR) (4), diastereoisomeric therebetween, while the ester (3) is converted into the mixture of epoxides (SR)+(SS)

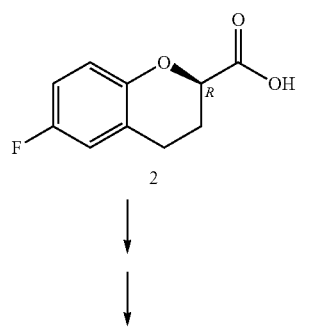

2

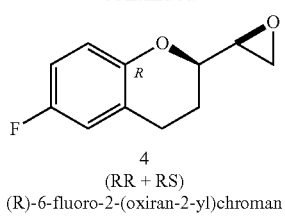

4
(RR + RS)
(R)-6-fluoro-2-(oxiran-2-yl)chroman

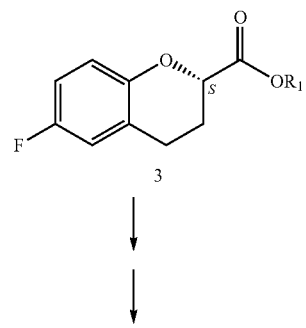

3

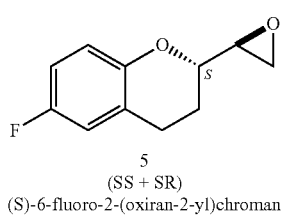

5
(SS + SR)
(S)-6-fluoro-2-(oxiran-2-yl)chroman (5).

By performing the reaction of opening of the mixture of epoxides (4) with benzylamine in a sterically hindered alcoholic solvent (such as isopropanol, sec-Butanol, tert-butanol, 2-methyl-2-butanol, isoamyl alcohol, 2-methyl-2-pentanol) it is had a kinetic resolution with formation of the sole amino alcohol RS (6), while the epoxide RR (7) is recovered as unchanged.

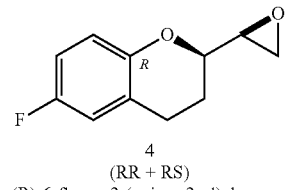

4
(RR + RS)
(R)-6-fluoro-2-(oxiran-2-yl)chroman

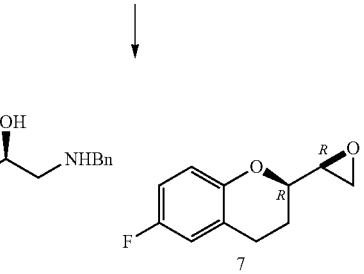

6   7

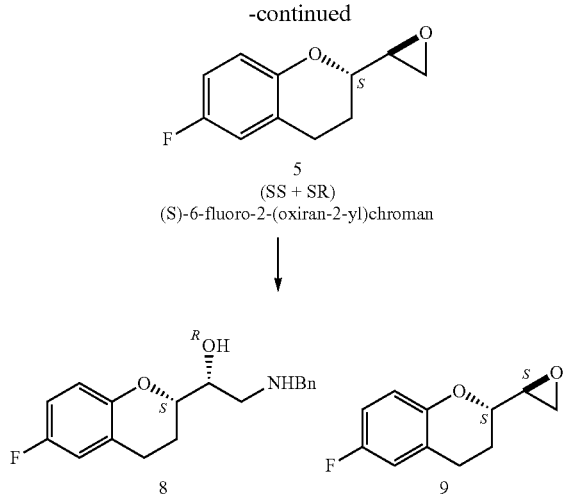

5
(SS + SR)
(S)-6-fluoro-2-(oxiran-2-yl)chroman

The same procedure, applied to mixture (5), produces amino alcohol SR (8) and epoxide SS (9).

Alternatively to the kinetic resolution described, the mixture of epoxides (4) may be chromatographically separated into the two epoxides RS and RR, and the mixture of the epoxides (5) into the two epoxides SR and SS; subsequently the epoxide RS is reacted with benzylamine obtaining the amino alcohol RS (6), while the epoxide SR is reacted with benzylamine to obtain the amino alcohol SR (8).

Finally, the reaction of the amino alcohol (6) with impurities constituted by unwanted diastereoisomeric compounds deriving from non-complete enantiomeric purity of the starting esters/acids), debenzylated and subsequently salified to obtain the desired final Nebivolol salt.

EXAMPLES

The invention is hereinafter described in detail by the following examples, purely by way of illustration and not for limitative purposes:

Example 1

As described in EP-0687305, a strain of recombinant *E. Coli* containing the esterase originally expressed in *Ophiostoma novo-ulmi* is cultivated according to techniques well-known to a person skilled in the art. A cell fraction is lysed by sonication and the lysate centrifuged to obtain a cell-free supernatant solution. 1.6 mL of solution containing the esterase (lipase) enzyme obtained from *Ophiostoma novo-ulmi* (6800 units/mL) and a suspension of about 25 g of ethyl 6-fluorochroman-2-carboxylic acid (1) in 25 mL of deionized water with 100 µL of Tween 80, are added to 500 mL of a 0.1N NaHCO$_3$ buffer solution (pH 9.7), optionally adjusting the pH with 2N NaOH to a value of 9.7. The mixture thus obtained is gently stirred.

pH is automatically maintained at the value of 9.7 with controlled additions of a 2N NaOH solution.

Evolution of the reaction is controlled by HPLC.

At the end of the hydrolysis reaction, the mixture is extracted with dichloromethane so as to obtain the ester in the

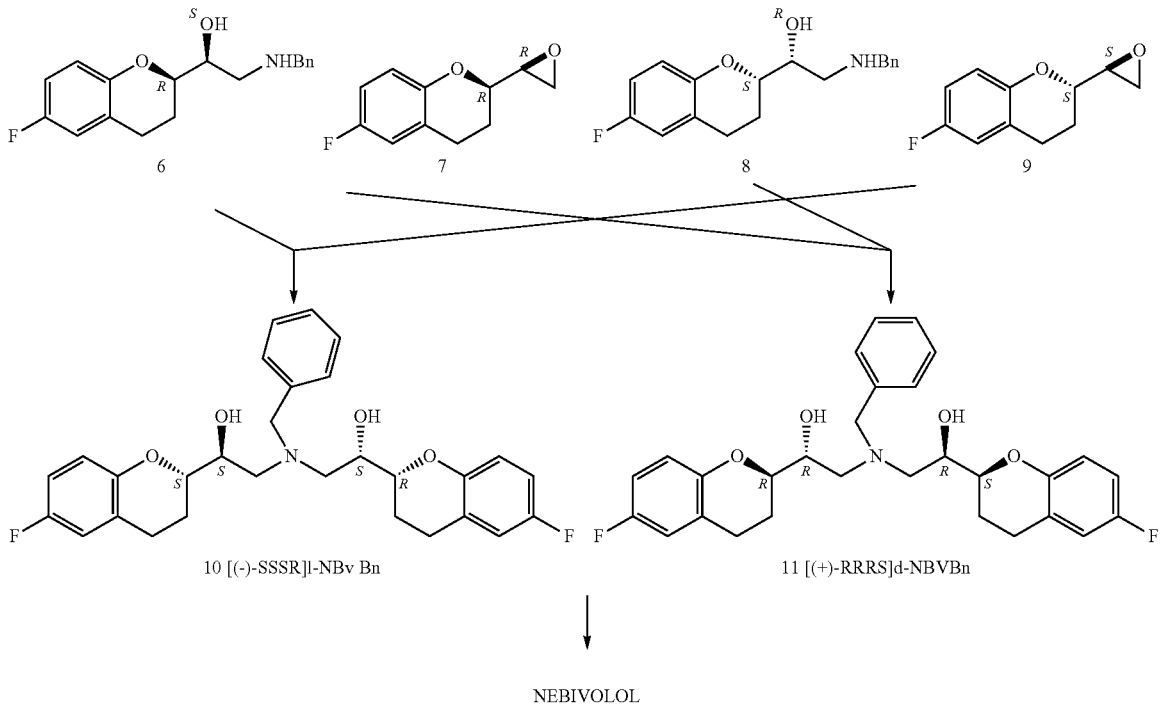

the epoxide (7) produces the N-benzylated derivative of l-Nebivolol (10), and analogously the reaction of the amino alcohol (8) with the epoxide (9) provides the N-benzylated derivative of d-Nebivolol (11).

The compounds (10) and (11) are pooled in equimolecular amounts, purified by crystallization (so as to eliminate any organic phase. The aqueous solution is acidified with 1N hydrochloric acid to pH 1, and then extracted with dichloromethane for recovery of the acid.

The two organic phases are separately washed with brine, and concentrated to obtain respectively 12.2 g of ethyl ester and 11.0 g of acid.

Enantiomers ratio (HPLC):

(S) ester (3)/(R) ester: 95.31/4.69

(R) acid (2)/(S) acid: 95.36/4.64

Evaluation of rotatory power in DMF at 25° C. for the mixture of acids (comprising the acid (2)) shows said mixture to be levorotatory and in accordance with what reported in EP0334429 for the R isomer.

ACID (2) 1H-NMR (DMSO-D6, 400 MHz): $\delta_H$. (ppm): 2.04 (2H, m, OCHCH$_2$CH$_2$), 2.64 (1H, m, OCHCH$_2$CH$_2$), 2.79 (1H, m, OCHCH$_2$CH$_2$), 4.75 (1H, t, J=4.5 Hz, OCHCO), 6.80-7.00 (3H, m, CHar), 13.00 (1H, b, COOH).

ETHYL ESTER (3) 1H-NMR (DMSO-D6, 400 MHz): $\delta_H$. (ppm): 1.19 (3H, t, J=7.2 Hz, CH$_3$), 2.04 (1H, m, OCHCH$_2$CH$_2$), 2.14 (1H, m, OCHCH$_2$CH$_2$), 2.62 (1H, m, OCHCH$_2$CH$_2$), 2.80 (1H, m, OCHCH$_2$CH$_2$), 4.86 (1H, t, J=4.5 Hz, OCHCO), 6.80-7.00 (3H, m, CHar)

Analysis process: Kromasil 5-AmyCoat (4.6×250 mm) column; eluents: (A) hexane (0.1% TFA), (B) isopropanol, isocratic (A)/(B) 85/15; flow: 1 mL/min, temperature: 40° C.; Detector: UV at 280 nm;

Example 2

Preparation of Acyl Meldrum Derivative

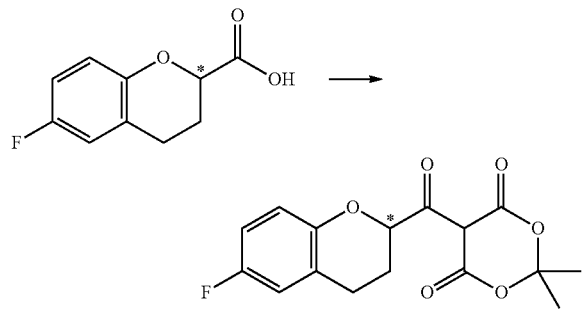

28 g of resolved (R) acid are solubilized in 250 mL anhydrous dichloromethane; to the resulting solution, 1.4 equivalents of oxalyl chloride and DMF dropwise are added. The solution is maintained under stirring at room temperature and under N$_2$; after 1.5 hours solvent is evaporated, obtaining an oil that is redissolved into 200 mL anhydrous dichloromethane. Separately, Meldrum's acid (1.05 equivalents) and pyridine (2 equivalents) are dissolved in anhydrous dichloromethane (150 mL) and left under stirring at 0° C. for 15 min. To this solution the previously formed acid chloride is added. At the end of the adding the mixture is left under stirring at 0° C. for 1 hour, and other 45 min at room temperature. Then, it is diluted with other 500 mL dichloromethane and the organic phase is washed with H$_2$O (2×200 mL), 2N HCl (100 mL), water, and brine, and dried on Na$_2$SO$_4$. An oil is obtained which is taken up with 20 volumes of diisopropyleter, obtaining a brown solid (40 g, HPLC purity=81%, $\lambda$=280 nm) which is filtered and dried. The obtained solid is used in the subsequent reaction without further purification.

Example 3

Preparation of β-Keto Ester

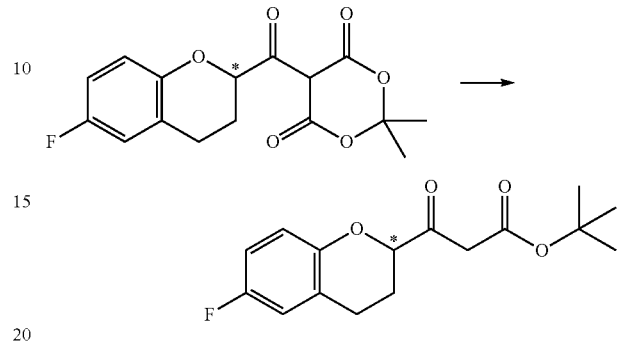

40 grams of crude acyl Meldrum derivative (R) are placed under stirring with 110 mL tert-butanol; the resulting mixture is heated to 80° C. for 1 h until a control by HPLC highlights the disappearance of the starting product. At the end of the reaction, tert-butanol is evaporated under reduced pressure; it is taken up with 500 mL ethyl acetate and the organic phase is washed with a saturated NaHCO$_3$ solution, H$_2$O to neutrality, brine and it is dried on Na$_2$SO$_4$. Then the solvent is evaporated, obtaining 28 g of crude β-keto ester (HPLC purity=69%, $\lambda$=280 nm) as an oil, which is used in the subsequent reaction without further purification.

Example 4

Preparation of Chloro β-Keto Ester

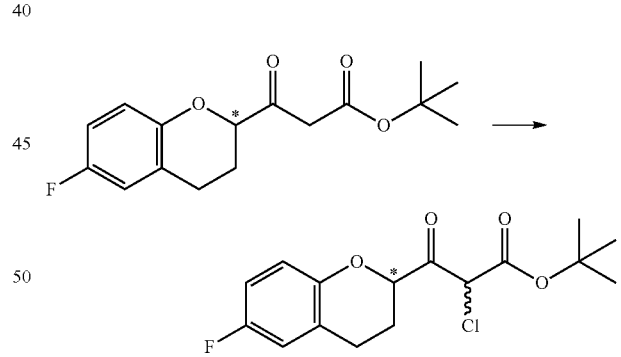

28 g of crude β-keto ester (R) are dissolved in 250 mL ethyl acetate, and to this solution 0.26 equivalents of Mg(ClO$_9$)$_2$ are added. After 30 min, 0.95 equivalents of N-chlorosuccinimide are added in 2 h. At the end of the addition, the resulting mixture is stirred for 1 hour at room temperature. Then the solid formed is eliminated, the clear solution is transferred into a separating funnel, after diluting with other 350 mL of ethyl acetate; the organic phase is washed with brine, H$_2$O, and dried on Na$_2$SO$_4$. The solvent is evaporated, obtaining 34 g of crude chlorine derivative (HPLC purity=79.40%, $\lambda$=280 nm) which is used in the subsequent reaction without further purification.

Example 5

Preparation of α-Clorochetone

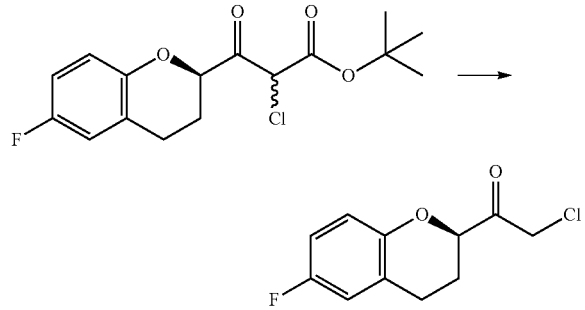

34 g of crude chloro β-keto ester (R) are refluxed with HCOOH (100 mL), CH₃COOH (120 mL) and H₂O (30 mL); after 1.5 h a control by HPLC highlights the end of the reaction. The mixture is then evaporated under reduced pressure, taken up with ethyl acetate, and the organic phase is washed with brine, saturated NaHCO₃, H₂O, and dried on Na₂SO₄. Then, the solvent is evaporated under reduced pressure, obtaining 21 g of α-chloro-ketone (HPLC purity=60%, λ=280 nm) as an oil that is used tel quel for the next step without further purification.

Example 6

Preparation of α-Chloroalcohol

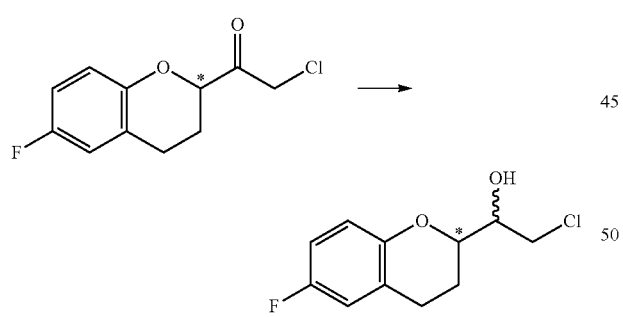

21 g of the oil obtained from the preceding reaction are dissolved in 15 volumes of MeOH, to this solution 2.0 equivalents of NaBH(OCOCH₃)₃ are added with a spatula, and it is kept under magnetic stirring at room temperature. After 45 min another equivalent of NaBH(OCOCH₃)₃ is added. After 1 hour from the last addition, a control by HPLC denotes the end of the reaction. The solvent is evaporated under reduced pressure, all is transferred into a separating funnel with ethyl acetate and the organic phase is washed with H₂O and brine, and dried on Na₂SO₄. There are obtained 21 g of an oil that is purified by flash chromatography (silica/crude ratio: 30:1, eluent: petroleum ether/AcOEt 92:8), obtaining 14.2 g of a chloro-alcohol (HPLC purity=86.5%, λ=280 nm).

Example 7

Preparation of (RR+RS) Epoxides (4)

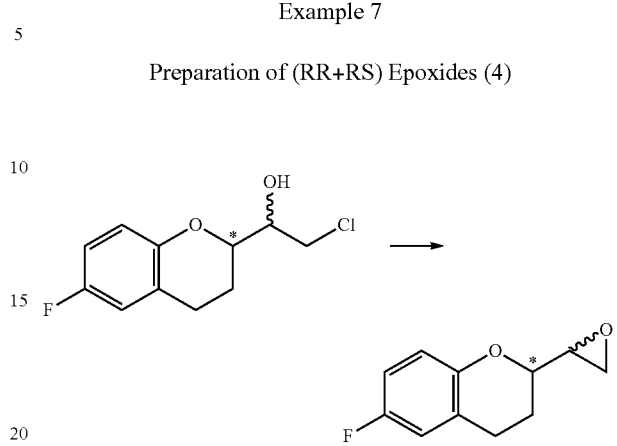

14 g of α-chloro-alcohol are dissolved in 20 volumes of anhydrous Et₂O, and to this solution 2.8 g of preceding NaH, washed with petroleum ether, are added. After 1 hour a control by TLC (silica gel, eluent: petroleum ether/AcOEt 85:15) denotes the disappearance of the starting chloro alcohol (one blot in TLC) and the formation of the two epoxides (two clearly distinct blots on TLC). The reaction mixture is then diluted with other 30 volumes of Et₂O, and all is poured in 100 mL of 1M NaHSO₄, maintaining a brisk stirring. The organic phase is washed with NaHCO₃, H₂O, brine, and dried on Na₂SO₄. The solvent is then evaporated under reduced pressure, obtaining 11.4 g of the mixture of epoxides as an oil (HPLC Purity>98%, λ=280 nm) in a ratio of 51:48.

The presence of only two main peaks in the ratios indicated in the analysis with chiral HPLC shows that no racemization was had in the reaction sequence going from the (R) acid to the mixture of diastereoisomeric (RR+RS) epoxides, with evident preservation of stereocenter chirality.

The mixture of (SR+SS) epoxides (5) is prepared analogously to what described in examples 2-7, starting from the ester (3) after its hydrolysis to the corresponding acid. In this case, the evaluation of the rotatory power in DMF at 25° C. for the acid thus obtained shows it as dextrorotatory and in accordance to what reported in EP 0334 429A1 for isomer S.

Example 8

Kinetic Resolution on the Mixture of (SS+SR) Epoxides

A solution of the mixture of (SS+SR) epoxides (4.50 g, 22.5 mmol) and benzylamine (3.8 mL, 35 mmol) in 2-methyl-2-butanol (38 mL) is mixed at room temperature for 12 hours. At the end of the reaction, formed (SR) amine 8 is filtered under vacuum and dried (1.90 g, 6.30 mmol). The filtered solution is poured in cyclohexane (250 mL) and the solution thus obtained is washed with 1M NaHSO₄ (100 mL) and H₂O (50 mL×2), and then concentrated under reduced pressure to obtain 1.30 (6.00 mmol) g of (SS) epoxide 9.

Kinetic resolution on the mixture of (RS+RR) epoxides is conducted analogously to what described in Example 8.

Example 9

Synthesis of l-Benzyl Nebivolol (SSSR)

The compound (RS)-2-benzylamino-1-(6-fluorochroman-2-yl)ethanol and the (SS) epoxide are dissolved in absolute ethanol (6 mL) and maintained at reflux until disappearance of the starting reagents. At the end of the reaction the mixture is left to reach room temperature and the solvent is removed under reduced pressure.

Example 10

Synthesis of d-Benzyl Nebivolol (RRRS)

The compound (SR)-2-benzylamino-1-(6-fluorochroman-2-yl)ethanol and the (RR) epoxide are treated as in Example 9 to obtain d-benzyl Nebivolol.

Example 11

Synthesis of d,l-Benzyl Nebivolol

The l-benzyl Nebivolol described in Example 9 (3.00 g) and the d-benzyl Nebivolol described in Example 10 (3.00 g) are pooled and the mixture thus obtained (6.0 g) is purified by crystallization, obtaining 5.0 g of N-benzyl Nebivolol (83%, HPLC purity=99.6%). During purification by crystallization there are eliminated also the impurities consisting of undesired isomers deriving from non-complete enantioselective hydrolysis of the starting ethyl 6-fluorochroman-2-carboxylic acid (1).

Example 12

Synthesis of Nebivolol Hydrochloride

The compound d,l-benzyl Nebivolol (5.0 g, 410 mmol) is dissolved in methanol (400 mL) together with 20% Pd(OH)$_2$/C (1% b/w). The mixture is maintained under stirring and under hydrogen atmosphere. At the end of the reaction the catalyst is filtered on a porous septum, and concentrated HCl (36 mL) is added to the filtrate. The solution is concentrated under reduced pressure and the residue obtained is heat-treated with absolute ethanol (50 mL). The obtained solid is filtered and dried under vacuum (1.0 g, yield: 82%, HPLC purity: 99.9%)

HPLC Analytical Method

| Column | Merck LiChrosphere 100 RP$_{18}$ endcapped (5 µm) (4.6 × 250 mm) |
|---|---|
| Eluent | A: water + 0.1% TFA, B: acetonitrile + 0.1% TFA Gradient: from 40% B to 90% B in 20 min + isocratic 90% B in 10 min |
| Injection volume | 20 µL |
| Flow | 1 mL/min |
| Detector | LC: UV. λ: 280 nm |
| Temperature | Room temperature |

The invention claimed is:

1. A method for the synthesis of d-Nebivolol and/or l-Nebivolol of the following formulas

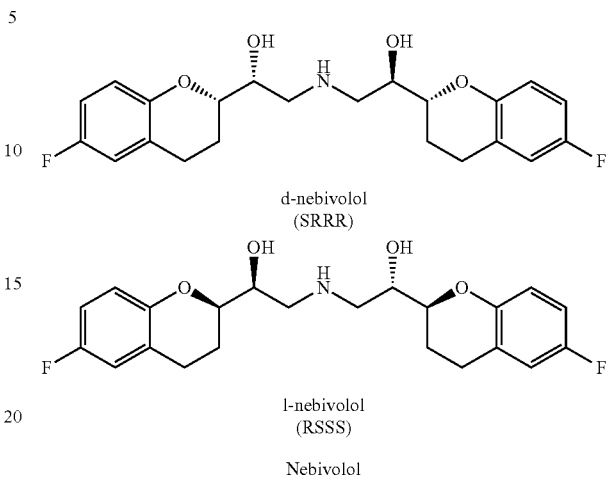

d-nebivolol (SRRR)

l-nebivolol (RSSS)

Nebivolol comprising the following steps:
a) hydrolyzing a mixture of enantiomers of the 6-fluoro-2-carboxylic acid ester (1), wherein R$_1$ is a linear or branched C$_{1-5}$ alkyl group

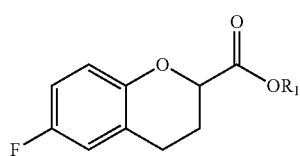
(1)

by a stereoselective enzymatic hydrolysis reaction to give a mixture of R acid (2) and S ester (3);

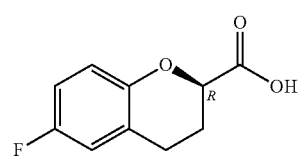
(2)

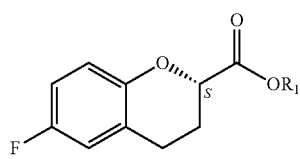
(3)

b) using thus obtained acid (2) and ester (3) for the synthesis respectively of mixtures of epoxides (RR) and (RS) (4) and (SS) and (SR) (5);

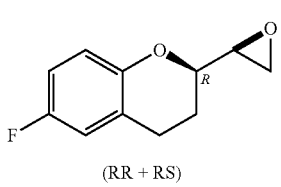
(4)

(RR + RS)

(5)

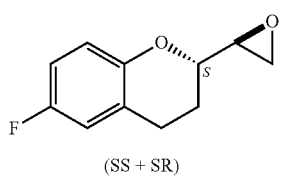

(SS + SR)

c) resolving the mixtures of epoxides (4) and (5) to obtain respectively amino alcohol RS (6)+epoxide RR (7) and amino alcohol SR (8)+epoxide SS (9);

(6)

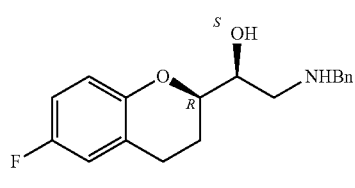

(7)

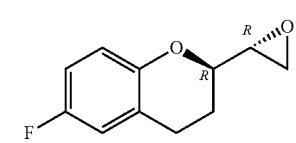

(8)

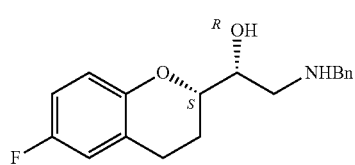

(9)

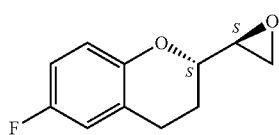

d) reacting amino alcohols (6) and (8) with epoxides (7) and (9) to obtain l-benzyl Nebivolol (10) and d-benzyl Nebivolol (11); and (10)

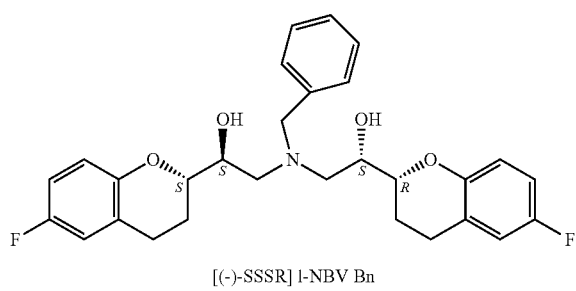

[(−)-SSSR] l-NBV Bn (11)

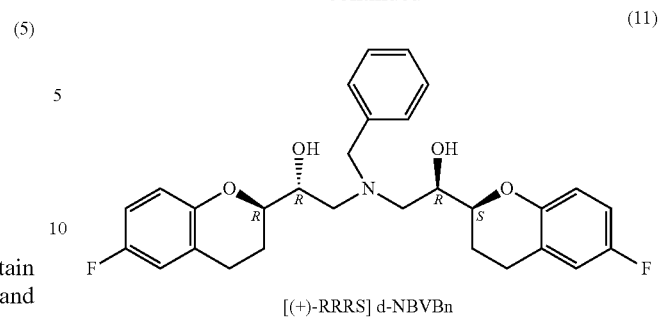

[(+)-RRRS] d-NBVBn e) removing the benzyl protecting group;

wherein in step (a), hydrolysis is carried out to give the mixture of R acid (2) with an enantiomeric excess of >70% and of S ester (3) with an enantiomeric excess of >70%; in step (c), the mixtures of epoxides (4) and (5) are kinetically resolved by reacting them with benzylamine in a sterically hindered alcohol; and the enzymatic hydrolysis reaction is carried out by an esterase obtained from genus *Ophiostoma*.

2. The synthesis method according to claim 1, wherein the enzymatic hydrolysis reaction is carried out by an esterase obtained from strain AJ3 of *Ophiostoma novo-ulmi*.

3. The method according to claim 1, wherein the enzymatic hydrolysis reaction is conducted at a pH between 8 and 11.

4. The method according to claim 3, wherein the enzymatic hydrolysis reaction is conducted at a pH between 8.5 and 10.

5. The method according to claim 1, wherein the enzymatic hydrolysis reaction is conducted at a temperature between 10° C. and 35° C.

6. The method according to claim 5, wherein the enzymatic hydrolysis reaction is conducted at a temperature between 20° C. and 25° C.

7. The method according to claim 1, wherein the enzymatic hydrolysis reaction is conducted in an aqueous environment or in the presence of water immiscible solvents.

8. The method according to claim 1, wherein the enzymatic hydrolysis of the mixture of esters (1) proceeds to yield a mixture of (R) acid (2) and (S) ester (3) with an enantiomeric excess of >80% or >90% in both components.

9. The method according to claim 1, wherein the acid (2) is converted into the mixture of RR+RS epoxides (4), whereas the ester (3) is converted into the mixture of SS+SR epoxides (5).

10. The method according to claim 1, wherein the kinetic resolution with benzylamine of the mixtures of epoxides (4) and (5) is conducted in a sterically hindered alcohol selected from the group consisting of sec-Butanol, tert-butanol, 2-methyl-2-butanol, isoamyl alcohol, and 2-methyl-2-pentanol.

11. The method according to claim 10, wherein the kinetic resolution with benzylamine of the mixture of epoxides (4) is conducted in a sterically hindered alcohol selected from the group consisting of sec-Butanol, tert-butanol, 2-methyl-2-butanol, isoamyl alcohol, and 2-methyl-2-pentanol, obtaining only the amino alcohol RS (6), while the epoxide RR (7) is recovered as unchanged.

12. The method according to claim 10, wherein the kinetic resolution with benzylamine of the mixture of epoxides (5) is conducted in a sterically hindered alcohol selected from the group consisting of sec-Butanol, tert-butanol, 2-methyl-2-butanol, isoamyl alcohol, and 2-methyl-2-pentanol, obtaining only the amino alcohol SR (8) while the epoxide SS (9) is recovered as unchanged.

13. The method according to claim 11, wherein the sterically hindered alcohol is 2-methyl-2-butanol.

14. The method according to claim 1, wherein the amino alcohol RS (6) is reacted with the epoxide SS (9) to give the l-benzylated Nebivolol (10) and/or the amino alcohol SR (8) is reacted with the epoxide RR (7) to give the d-benzylated Nebivolol (11).

15. The method according to claim 14, wherein the compounds (10) and (11) are mixed in a 1:1 ratio, deprotected from the benzyl group to give the final product Nebivolol.

16. The method according to claim 1, wherein the final product Nebivolol is salified with hydrochloric acid, obtaining the corresponding hydrochloride.

* * * * *

UNITED STATES PATENT AND TRADEMARK OFFICE
CERTIFICATE OF CORRECTION

PATENT NO. : 9,090,922 B2  Page 1 of 1
APPLICATION NO. : 13/990220
DATED : July 28, 2015
INVENTOR(S) : Mauro et al.

It is certified that error appears in the above-identified patent and that said Letters Patent is hereby corrected as shown below:

Specification

1. Replace "2007/041805" with --2004/041805-- at column 6, line 60.

2. Delete "(Scheme 5)" at column 6, line 67.

3. Replace "Scheme 6," with --Scheme 5-- at column 7, line 57.

4. Replace "Scheme 7" with --Scheme 6-- at column 8, lines 61-2.

5. Replace "WO2007041805" with --WO 2008/010022-- at column 17, line 49.

Signed and Sealed this
Nineteenth Day of January, 2016

Michelle K. Lee
*Director of the United States Patent and Trademark Office*